United States Patent [19]
Durgin, Jr. et al.

[11] Patent Number: 5,522,815
[45] Date of Patent: *Jun. 4, 1996

[54] INTEGRATED CATHETER FOR DIVERSE IN SITU TISSUE THERAPY

[76] Inventors: Russell F. Durgin, Jr., 146 Knott St., Attelboro, Mass. 02073; Christopher A. Rowland, 171 Stern Rd., Marlborough, Mass. 01752; Roy H. Sullivan, 302 Sutton St., Uxbridge, Mass. 01569; Michael G. Vergano, 12 Crestwood Ct., Cumberland, R.I. 02864

[*] Notice: The term of this patent shall not extend beyond the expiration date of Pat. No. 5,336,220.

[21] Appl. No.: 287,956

[22] Filed: Aug. 9, 1994

Related U.S. Application Data

[63] Continuation of Ser. No. 63,094, May 14, 1993, Pat. No. 5,336,222, which is a continuation-in-part of Ser. No. 38,903, Mar. 29, 1993, Pat. No. 5,403,311.

[51] Int. Cl.⁶ ..................................................... A61B 17/39
[52] U.S. Cl. ........................ 606/50; 606/49; 606/41; 604/21

[58] Field of Search ........................ 606/37–42, 45–50; 604/21, 22; 607/104, 105, 115, 116, 120, 122

[56] References Cited

U.S. PATENT DOCUMENTS 5,336,222  8/1994  Durgin, Jr. et al. .................... 606/50

Primary Examiner—Stephen C. Pellegrino
Assistant Examiner—Michael Peffley
Attorney, Agent, or Firm—Pearson & Pearson

[57] ABSTRACT

An integrated catheter assembly for enabling diverse in situ therapies includes a catheter with an irrigation fluid lumen, a distal tip portion that acts as a hemostat and a needle for injection therapy that extends through the catheter lumen and a lumen in the distal tip portion. A needle hub structure carries the catheter and provides a sealing entrance for a needle that can be displaced between extended and retracted positions. The needle and electrodes are electrically isolated. The apparatus provides a physician the options of irrigating tissue, cauterizing tissue or injecting tissue without the need for removing the apparatus from the working channel of an endoscope.

20 Claims, 3 Drawing Sheets

INTEGRATED CATHETER FOR DIVERSE IN SITU TISSUE THERAPY

CROSS REFERENCE TO RELATED APPLICATION

This application is a continuation, of application Ser. No. 08/063,094, filed May 14, 1993, now U.S. Pat. No. 5,336,222, which is a continuation-in-part of Ser. No. 08/038,903 filed Mar. 29, 1993 for Electro-Coagulation, Ablation and Other Electro-Therapeutic Treatments of Body Tissue, now U.S. Pat. No. 5,403,311, which application is assigned to the same Assignee as the present invention.

BACKGROUND OF THE INVENTION

1. Field of the Invention

This invention generally relates to electro-coagulation of tissue in the body in combination with other forms of therapy using catheters.

2. Description of Related Art

It is very important to minimize the time required to stop internal bleeding in a patient. A physician has several medical instruments in his or her armamentarium for stopping such internal bleeding. In accordance with one modality that is particularly suited for bleeding into the gastrointestinal tract, a physician initially positions a flexible endoscope in the patient with its distal end proximate a hemorrhaging vessel. The physician may insert an irrigator through a working channel in the endoscope to clear the area by administering saline solution as a precursor to any attempts to stop bleeding. If the instrument being used for irrigation is like the Gold Probe™ hemostat manufactured by Boston Scientific Corporation, the assignee of this invention, the physician may then cauterize the bleeding vessel using a distally positioned hemostat. Such instruments are constructed to be employed through a working channel of an endoscope to seal potential bleeding sites as in the gastrointestinal tract or the esophagus. Other hemostats use mono-electropolar electrodes in which one electrode is carried by a catheter to a site while the other electrode is an exterior ground plate placed in a patient. Alternatively the physician may retract the irrigating catheter and insert an elongated needle through the endoscope to inject a vasoconstrictor into the vessel to slow hemorrhaging. Then the physician could remove the elongated needle and reinsert the hemostat to finish the operation.

The above-mentioned Gold Probe™ hemostat is an example of a device that supplies a suitable current density and wave form of radiofrequency energy to perform electro-coagulation or cauterization. It utilizes a catheter with a bipolar electrode assembly located on a distal flexible tip formed of a ceramic cylinder having a hemispherical end. The ceramic tip includes a pair of spaced gold spiral electrodes applied to its cylindrical surface and domed end. RF energy applied to the electrodes produces a current through adjacent tissue that heats and cauterizes the hemorrhaging vessel which is contacted by the tip of the catheter.

Notwithstanding the fact that both hemostasis and injection needle therapy are usually done on an emergency basis, the exchange of catheters to provide different functions continues and increases the risk to the patient because the time to complete therapy is extended. Extending the time to complete the therapy also increases patient discomfort. Consequently, physicians have to weigh the time, complexity and benefits of interchanging single or dual purpose catheters to change treatment modalities against whatever disadvantage may result by working with a single modality and single catheter.

Co-pending application Ser. No. 08/038,903 that is incorporated herein by reference provides a catheter generally characterized by an axially displaceable probe that acts as one of two electrodes for performing hemostatic therapy. The other electrode is spaced proximally from and is insulated with respect to the probe. The catheter has a lumen for administering irrigating fluids to tissue at the hemorrhaging vessel. In some embodiments irrigation fluid passes between the main probe and a structure at the distal end of the catheter. In other applications the distal tip portion includes separate passages for allowing an irrigating solution to pass into the area of the hemorrhaging vessel. In still another embodiment the irrigation fluid passes directly through the probe that comprises a hollow needle that also acts as an electrode and as an injection needle for administering a vasoconstrictor or other therapeutic agent into a bleeding vessel.

This apparatus, therefore, in its various embodiments, enables a physician to irrigate tissue and to treat a hemorrhaging vessel with injection therapy or hemostatic therapy without removing the catheter apparatus from the working channel or lumen of an endoscope. However, many physicians are familiar with standard devices such as the Gold Probe hemostat. One particular embodiment of Ser. No. 08/038,903, that is applied to a Gold Probe hemostat discloses a probe tip with two separate electrodes and an extensible conductive probe that provides a physician alternatives for hemostatic therapy. In accordance with one option the probe tip electrodes constitute bipolar electrodes and the extensible conductive probe is inactive electrically. In accordance with the other option the extensible probe is active and one or both of the probe tip electrodes act as a second electrode. This approach can complicate the apparatus required for connecting an RF generator source to the electrodes and related circuitry and can also increase the burden on the physician using the apparatus. Moreover, such procedures differ from those familiar to the physician as a result of use of prior art devices, so such a catheter assembly can impose other complications.

SUMMARY

Therefore it is an object of this invention to provide an integrated catheter assembly that enables a physician to select among hemostatic and injection therapies.

Another object of this invention is to provide an integrated catheter assembly that enables a physician to irrigate tissue selected for treatment and to optionally select between hemostatic and injection therapy.

Still another object of this invention is to provide an integrated catheter assembly that facilitates therapy of bleeding vessels and that simplifies the required procedures for such therapy.

Yet another object of this invention is to provide an integrated catheter assembly that enables a physician wide flexibility in the treatment of hemorrhaging vessels and that utilizes the standard operating characteristics of conventional single purpose or dual purpose assemblies.

In accordance with this invention, an integrated catheter assembly that enables a physician to utilize diverse in situ therapy modalities at selected tissue sites includes catheter, bipolar electrode tip and injection needle structures. A lumen extends from a proximal end to a distal end of the catheter structure to provide a passage from a location externally of the patient to the tissue being treated. The bipolar electrode structure attaches to the distal end of the catheter structure and provides hemostatic therapy to selected tissue. The electrode structure additionally has a central lumen aligned with the catheter lumen for enabling the transfer of irrigation fluids to tissue being treated. The injection needle structure is electrically isolated from the bipolar electrode means and extends from a proximal end externally of the patient through the lumens in the catheter and the bipolar electrode structure for axially displacement relative to the catheter and bipolar electrode structures. The needle structure can be extended distally beyond and can be retracted proximally of a distal end surface of the bipolar electrode structure.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
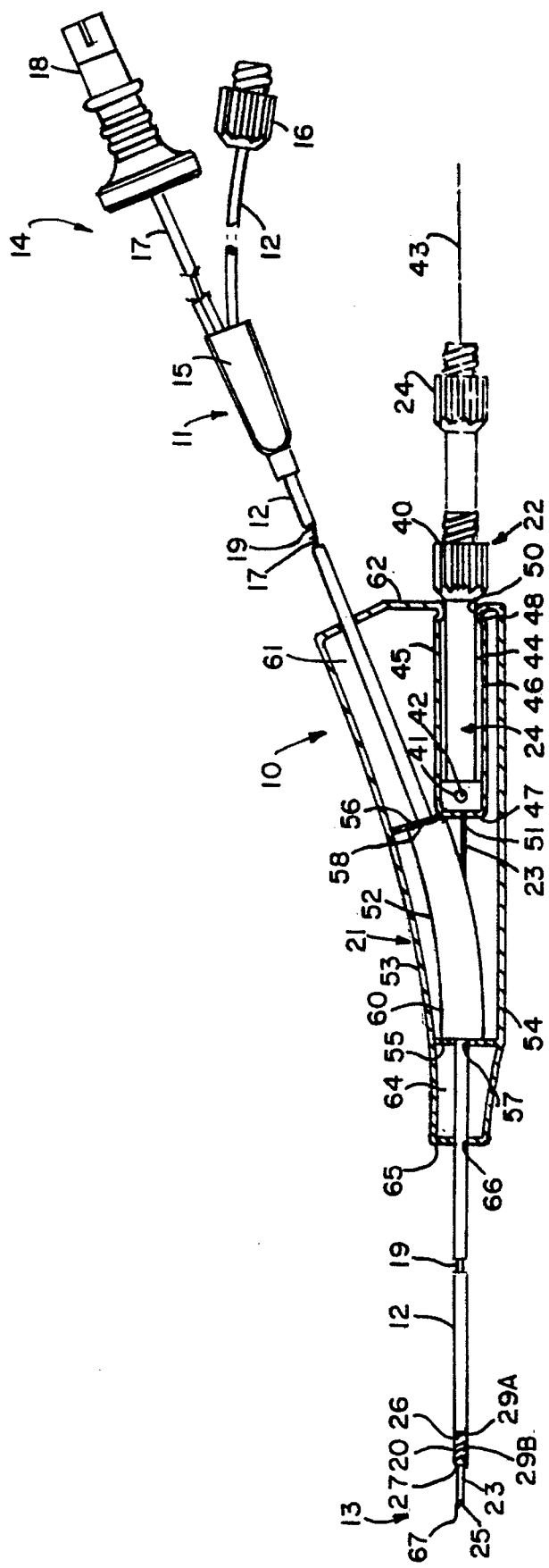
FIG. 1 is a view, partially in section, of an integrated catheter assembly extending between proximal and distal end portions that includes a catheter, an injection needle and a bipolar electrode assembly.

FIG. 1 discloses an integrated catheter assembly 10 that enables a physician to utilize diverse in situ therapy modalities at selected tissue sites without withdrawing the assembly 10 from the working channel or lumen of an endoscope. It includes a modified bipolar hemostat and irrigation system 11, such as the above identified Gold Probe hemostat. The system 11 enables a physician to utilize a dual purpose device for bipolar hemostasis and irrigation in the treatment of a bleeding vessel. The system 11 particularly includes a catheter 12 with a single lumen that extends from a distal location 13 to a proximal location 14. At the proximal location 14 a catheter hub 15 carries the catheter 12 from a Leur lock or similar catheter fitting 16 toward the distal location 13. Electrical leads 17 from an RF generator connector 18 also enter the catheter hub 15. RF generators of the type utilized with this apparatus are well known and therefore not shown. The electrical leads 17 are led into the center of the catheter 12 in the hub 15 thereby to be carried through a central lumen 19 of the catheter 12 to the distal location 13 and a bipolar electrode assembly 20. As an alternative, the catheter 12 may incorporate electrical leads in the catheter wall thereby to eliminate any contact between irrigating solutions in the lumen 19 and the electrical leads 17. The bipolar electrode assembly 20, when energized over the electrical leads 17 that connect the bipolar electrode assembly 20 with the RF generator (not shown) through the RF generator connector 18, provides hemostatic therapy by heating the tissue due to the inherent resistance of the tissue. Thus the electrical leads 17 and the RF generator connector 18 provide a connection between the RF electrode assembly 20 and the RF generator (not shown) to enable the user to control the energization of the RF electrode assembly 20 and the heating of the tissue engendered thereby.

In accordance with this invention, a needle hub 21 directs the catheter 12 therethrough and supports the proximal end of a needle assembly 22 that includes an injection needle 23. The injection needle 23 can move between extended and retracted positions by manipulation of an operator 24. The operator 24 is shown at its extended position in FIG. 1 by the solid lines and in its retracted position by phantom operator 24'. When the needle 23 extends distally beyond the distal end of the bipolar electrode assembly 20 as shown in FIGS. 1 and 3, it can penetrate tissue and enable a physician to administer a vasoconstrictor or similar agent through a lumen 25 in the injection needle 23.

Figure 2:
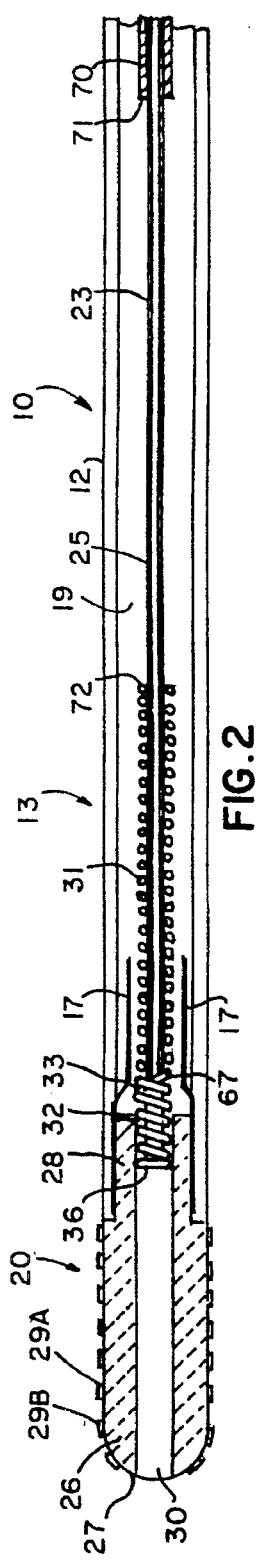
FIG. 2 is a detailed view, partially in section, of the distal end portion of the apparatus in FIG. 1 including the bipolar electrode assembly in which the injected needle is retracted.
Figure 3:
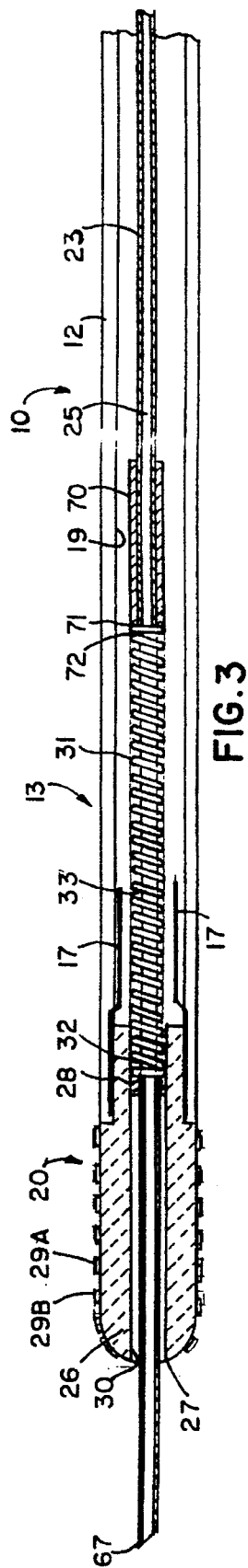
FIG. 3 is a detailed view, partially in section, of the distal end portion of the apparatus in FIG. 1 in which the injection needle is extended.

Referring now to different sections of the apparatus shown in FIG. 1 in more detail, FIGS. 2 and 3 depict a distal end location 13 of the integrated catheter assembly 10. In each of FIGS. 2 and 3 the distal end of the catheter 12 terminates at the bipolar electrode assembly 20.

More specifically the bipolar electrode assembly 20 includes a cylindrical body portion 26 having a hemispherical distal end tip 27 and a proximally extending shank 28 at its other end. Discrete spiral electrodes 29A and 29B are disposed on the outer surface of the body portion 26 and the end tip 27 and connect to the electrical leads 17. A distal tip lumen 30 extends through the body portion end tip 27 and shank 28. The shank 28 is nested and supported by the catheter 12.

Still referring to FIGS. 2 and 3, a needle guide portion 31 includes an end section 32 that is located in the proximal end of the lumen 30 and coextensive with a portion of the shank 28. The needle guide portion 31 extends proximally from the shank 28 and constitutes a pervious guide tube for the needle 23. More specifically, the needle guide 31 is formed as a spring with multiple spaced turns that define inter-turn passages 33. These passages 33 allow fluid to transfer from the catheter lumen 19 and through the distal tip lumen 30 to exit from the end tip 27. Fluid flow is relatively unimpeded in the structure shown in FIG. 2 when the injection needle 23 is retracted. The extension of the needle 23 to the position shown in FIG. 3 restricts the distal tip lumen 30, but flow can still occur.

Figure 4:
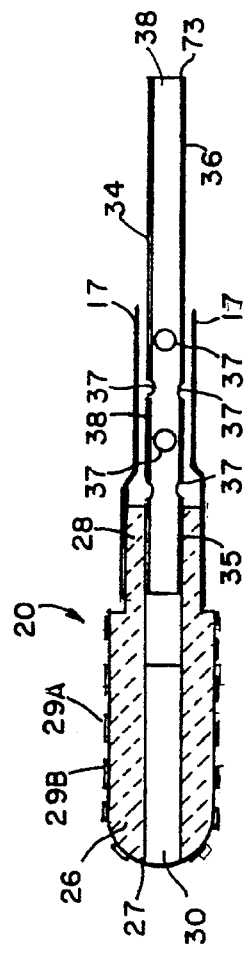
FIG. 4 depicts an alternate tip structure that can be substituted for the bipolar electrode assembly shown in FIGS. 2 and 3.

FIG. 4 depicts an alternative embodiment for the bipolar electrode assembly 20. In this particular embodiment, a tube 34 replaces the spring 31. The tube 34 has a section 35 that fits in the lumen 30 and is coextensive with a portion of the shank 27 and another section 36 that is proximal of the shank 27. This second section 36 includes a plurality of radially extending apertures 37 that act as passages for irrigation fluids from the catheter 12 through a central lumen 38.

Thus each of FIGS. 2 through 4 depict alternative embodiments of a bipolar electrode assembly 20 that includes first and second electrodes 29A and 29B for providing hemostatic therapy. In each embodiment a body portion 26 has a hemispherical distal end 27 and carries the electrodes 29A and 29B. A shank 28 extends proximally of the body portion 26 for insertion of the lumen 19 at the distal end of the catheter 12. A tubular pervious needle guide 31 extends proximally from the shank portion 28 in the lumen 19 to be coextensive with the distal portion of the catheter 12 for supporting the distal end of the injection needle 23 particularly in its retracted position.

Referring to FIG. 1, the operator 24 associated with the needle assembly 22 includes a proximal end fitting 40 that can connect to a syringe or other apparatus for enabling the injection of a vasoconstrictor or other therapeutic agent through the needle lumen 25. At its opposite end, the operator 24 includes a collar 41 and set screw 42 or other attaching apparatus for affixing the operator 24 to the needle 23. Such apparatus is known in the art. In this particular embodiment the operator 24 and needle 23 lie along an axis 43.

The needle hub 21 can be molded or otherwise formed to include a proximal compartment 44 defined by side walls 45 and 46 and end walls 47 and 48. An aperture 50 through the end wall 48 accommodates the operator 24 while an aperture 51 at the distal end wall 47 accommodates the needle 23. The end walls 47 and 48 support the proximal end of the needle assembly 22 and limit the range of travel of the operator 24 along the axis 43 between the position shown in FIG. 1 wherein the collar 41 abuts the wall 47 and a retracted position in which the collar 41 abuts the end wall 50.

An intermediate compartment 52 disposed distally of the proximal compartment 44 supports the catheter 12 in a radiused orientation. Curved and straight side walls 53 and 54 of the needle hub 21 and transverse end walls 55 and 56 define the compartment. The end wall 55 extends between the side wall 53 and 54; the end wall 56, between the side wall 53 and the intersection of the side wall 45 and end 47. Apertures 57 and 58 in the end walls 55 and 56 respectively capture the catheter 12.

An elastomeric seal 60 surrounds the catheter 12 and is located in the intermediate compartment 52. The needle 23 penetrates the seal 60 and the wall of the catheter 12 thereby to be located in the catheter lumen 19 to extend through the distal tip 30 as shown in FIG. 2. The seal 60 prevents leakage from the catheter 12 even during axial displacement of the needle 23 along the axis 43. This seal 60 generally will be formed of an elastomeric material and can take any of several forms as known in the art.

The needle hub 21 includes another proximal compartment 61 adjacent the proximal compartment 44. The compartment 61 is formed by a proximal end wall 62, the side walls 45 and 53 and the end wall 57. The end walls 57 and 62 in this compartment 61 support the catheter 12 proximally of the seal 60 and, with the compartment 52 and end wall 55, provides an angular offset to the catheter 12 with respect to the axis 43.

A distal compartment 64 is formed by the side walls 53 and 54, the end wall 55 and a distal end wall 65. An aperture 66 in the end wall 65 holds the catheter 12. The end walls 55 and 65 thereby maintain the alignment of the catheter 12 along the axis 43 to facilitate the placement and containment of the needle 23 within the catheter 12 lumen 19 distally of the needle hub 21.

Figure 5:
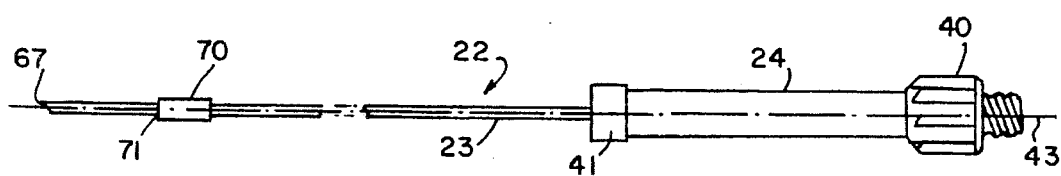
FIG. 5 is a detailed plan view of an injection needle used in the structure shown in FIGS. 1 through 3.

Still referring to FIG. 1, it is desirable to manufacture the needle hub 21 as a standard unit for a variety of applications. In some applications, the limits imposed on the axial travel of the injection needle 23 by the end walls 47 and 48 may allow an extension of the needle 23 from the bipolar electrode assembly 20 that is greater than desired. It is possible to customize that extension by applying a positive stop structure to the injection needle assembly 22. One such structure is shown in FIGS. 2, 3 and 5 where like numbers refer to like elements. As shown the needle assembly 22 particularly in FIG. 5 includes the operator 24 with its end fitting 40 and collar 41. The injection needle 23 extends as a constant diameter tube to its distal end 67. A collar 70 having a distal, radially extending end surface 71 is located on the needle 253 at some predetermined location spaced from the distal end 67 by a distance that equals the length of the desired extension plus the distance between the end tip surface 27 of the bipolar electrode assembly 20 as shown in FIG. 1 and a proximal end 72 of the needle guide 31 as shown in FIGS. 2 and 3. Consequently as the injection needle 23 moves from its retracted position in FIG. 2 to its extended position in FIG. 3, the distal end surface 71 of the collar 70, that overlies the spring 31, abuts the end 72 and prevents any further distal extension of the needle 23. If the bipolar electrode assembly 20 of FIG. 4 were used, the end surface 71 would abut an end surface 73 on the tube 34.

Figure 6:
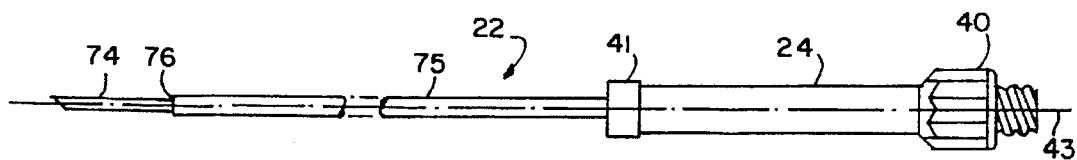
FIG. 6 is a detailed plan view of an alternate embodiment of an injection needle.

FIG. 6 discloses an alternative stop mechanism wherein the needle assembly 22 includes an operator 24 with proximal end connector 40 and distal collar 41. In this embodiment the needle assembly 22 comprises a distal hollow section 74 and a proximal hollow section 75. The distal section 74 has a given diameter corresponding to the diameter of the needle 23 shown in FIG. 5 and determined by the application requirements. The length of the distal section 74 equals the desired extension of the needle plus the distance from the distal end tip 27 to either end surface 72 of the spring 31 in FIGS. 2 and 3 or the end surface 73 of the tube 34 in FIG. 4. The proximal section 75 extends from the distal portion 74 to the operator 24 and has a larger diameter. Consequently the proximal portion 75 forms an annular radial surface 76 at its distal end that also will abut either the end 72 of the spring 31 in FIGS. 2 and 3 or the end 73 of the needle guide tube 34 shown in FIG. 4.

When a physician needs to treat a patient with internal bleeding, the physician will, as in the prior art, insert an endoscope with a working channel. Then the physician can insert the integrated catheter apparatus 10 shown in FIG. 1 through the working channel, normally with the injection needle in its retracted position (as shown in FIG. 2). If it is necessary to irrigate the area, the physician can apply irrigating fluid through the connector 16 and the catheter lumen 19 to be ejected at the distal end tip 27 through the lumen 30 as shown in FIGS. 2 and 3. If upon viewing the site the physician decides to utilize hemostasis, it is merely necessary to position the bipolar electrode assembly 20 at the tissue and energize the electrodes 29A and 29B. The needle assembly 22 has no effect on this process. If, on the other hand, the physician determines the injection of a vasoconstrictor is appropriate before or in lieu of hemostasis, the physician can easily extend the injection needle 23 and administer a therapeutic agent through the connector 40 and the needle 23. Thereafter the physician can irrigate the site at will and elect to use hemostasis in addition to injection therapy. All these decisions are made and elections pursued without withdrawing the integrated catheter apparatus 10 from the endoscope. Moreover, each component requires the same basic manipulations as prior art devices familiar to a physician. Consequently time otherwise lost in manipulating individual elements in and out of the endoscope or in assuring proper operation of other combined apparatus is eliminated. This reduces the time for therapy and decreases the discomfort of the patient.

It will be helpful to describe some specific embodiments of this invention for the purpose of further understanding the construction and use of this invention. In certain specific embodiments, for example, the catheter assembly 10 can comprise a 7 Fr. or 10 Fr. catheter 20 and a 21 gauge needle 23. In an another embodiment, using a needle as shown in FIG. 6, the distal needle portion comprises a 23–25 gauge tubular structure while the proximal portion comprises a 21 to 22 gauge tubular structure. In addition, one embodiment of the catheter assembly 10 in FIG. 1 extends about 250 cm. between the distal tip portion 13 and the hub 21 while the extension of the needle 23 from the bipolar electrode assembly is limited to a maximum of 6 mm.

Although this invention has been described in terms of a specific embodiment, and certain modifications, still other modifications can be made. For example, needle assembly 22 can comprise a one-piece metal structure in the form shown in FIG. 5. In the form shown in FIG. 6 the distal portion might be constructed of a metal while the proximal portion 75 might be constructed of plastic. The needle assembly 22 also may include means for preventing rotation about the axis 43 during use. Thus it will be apparent that these and other modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A catheter assembly for enabling a physician to utilize diverse in situ therapy modalities at selected tissue comprising:

A. catheter means having a lumen therethrough from a proximal to a distal end thereof for extending from a location externally of a patient to tissue being treated, B. heating means attached to the distal end of said catheter means for providing therapy to the selected tissue, said heating means having a lumen therethrough aligned with said catheter means lumen for enabling the transfer of fluids between said catheter means lumen and the selected tissue through said heating means lumen, and C. needle means for providing injection therapy extending from a proximal end externally of the patient through said lumens in said catheter means and said heating means for axial displacement whereby a distal portion of said needle means extends distally beyond and retracts proximally of a distal end surface of said heating means.

2. A catheter assembly as recited in claim 1 wherein:

i. said catheter means includes control means for connecting said heating means, a catheter with a lumen through which said needle means extends, and catheter hub means at the proximal end of said catheter for carrying said catheter and for directing said connecting means through said catheter whereby said connecting means are carried to said heating means, and ii. said heating means includes a heating element, a body portion having a distal end for carrying said heating element, a shank portion extending proximally of said body portion for connection with the distal end of said catheter, and a cylindrical needle guide portion extending proximally from said shank portion to be coextensive with a distal portion of said catheter for supporting the distal end of said needle means in its retracted position.

3. A catheter assembly as recited in claim 2 wherein said needle guide portion is pervious thereby to enable the transfer of fluid between said catheter lumen and said lumen in said heating means.

4. A catheter assembly as recited in claim 3 wherein said needle guide portion comprises an elongated tube having one end portion inserted into said means lumen at the proximal end thereof and at least one radial aperture through said tube proximally of said electrical element for enabling the fluid transfer.

5. A catheter assembly as recited in claim 3 wherein said needle guide portion comprises an elongated spring with axially spaced turns inserted into said heating means lumen at the proximal end thereof whereby the fluid transfer occurs between adjacent turns of said spring.

6. A catheter assembly as recited in claim 2 wherein needle means includes:

i. an elongated needle having a lumen therethrough, ii. operator means at the proximal end thereof for facilitating the transfer of fluid to said needle lumen, and iii. needle hub means attached to said catheter intermediate said catheter hub means and said distal end of said catheter for guiding said elongated needle into said catheter lumen.

7. A catheter assembly as recited in claim 6 wherein said needle hub means includes proximal compartment means for receiving and interacting with said operator means for displacement to enable the extension and retraction of said elongated needle, said proximal compartment means including means for limiting proximal movement of said operator means.

8. A catheter assembly as recited in claim 7 wherein said needle hub means includes an other compartment means disposed distally of said proximal compartment means for supporting said catheter in a radiused orientation and sealing means disposed in said other compartment means and around said catheter means for enabling said needle means to penetrate said sealing means and said catheter into said catheter lumen thereby to be movable between said extended and retracted positions.

9. A catheter assembly as recited in claim 6 wherein said needle hub means additionally includes a plurality of axially aligned compartment means including proximal compartment means and an other compartment means disposed distally of said proximal compartment means for supporting said catheter in a radiused orientation and sealing means disposed in said second compartment means and around said catheter means for enabling said needle means to penetrate said sealing means and said catheter into said catheter lumen thereby to be movable between said extended and retracted positions.

10. A catheter assembly as recited in claim 9 wherein needle means includes stop means at a predetermined location spaced from the distal end of and formed on said elongated needle for engaging the proximal end of said shank portion thereby to limit the extension of said elongated needle from the distal tip of said heating means.

11. A catheter assembly as recited in claim 10 wherein said stop means comprises a collar means formed with a distal end positioned at the predetermined location.

12. A catheter assembly as recited in claim 10 wherein said elongated needle is formed of a distal portion of a given diameter that extends to the predetermined location and a proximal portion that extends from the predetermined location proximally to said operator means, said proximal portion having a greater diameter than said distal portion thereby to form a radially extending annular stop surface for engaging the proximal end of said shank means.

13. A catheter assembly as recited in claim 6 wherein said needle hub means includes a proximal compartment means for receiving said operator means, an intermediate compartment means for supporting said catheter in a radiused orientation, distal compartment means for constraining a portion of said catheter and sealing means disposed in said intermediate compartment means and around said catheter means for enabling said needle means to penetrate said sealing means and said catheter into said catheter lumen thereby to be movable between said extended and retracted positions.

14. A catheter assembly for enabling a physician to utilize diverse in situ therapy modalities for selected tissue comprising:

A. heating means for providing therapy to the selected tissue, said heating means including:
        i. a heating element,
        ii. a body portion having a distal end for carrying said heating element,
        iii. a shank portion extending proximally of said body portion, said body and shank portions being formed about a central axis and defining an axially extending lumen therethrough that is open at the distal and proximal ends of said heating element, and
        iv. a cylindrical pervious needle guide portion extending proximally from said shank portion,
    B. catheter means having a lumen therethrough from a proximal to a distal end thereof for extending from a proximal location externally of a patient to the selected tissue, said catheter means including:
        i. a catheter with a lumen therethrough for enabling the transfer of irrigation fluids, said distal end of said catheter overlying and supporting said shank portion,
        ii. catheter hub means at the proximal end of said catheter for carrying said catheter, and
        iii. connection means connected to said heating element and extending distally therefrom through said catheter and through said catheter hub means for controlling said heating element,
    C. needle means for providing injection therapy including:
        i. an elongated needle having a lumen therethrough,
        ii. operating means at the proximal end of said elongated needle means,
        iii. needle hub means attached to said catheter intermediate said catheter hub means and said distal end of said catheter for guiding said elongated needle into said catheter lumen whereby said needle extends distally within said catheter lumen, and
        iv. stop means at a predetermined location spaced from the distal end of and formed on said elongated needle for engaging the proximal end of said shank portion thereby to limit the extension of said elongated needle from the distal tip of said heating means.

15. A catheter assembly as recited in claim 14 wherein said needle guide portion comprises an elongated tube having one end portion inserted into said heating means lumen at the proximal end thereof and at least one radial aperture through said tube proximally of said heating element for enabling the fluid transfer.

16. A catheter assembly as recited in claim 14 wherein said needle guide portion comprises an elongated spring with axially spaced turns inserted into said heating means lumen at the proximal end thereof whereby the fluid transfer occurs between adjacent turns of said spring.

17. A catheter assembly as recited in claim 14 wherein said stop means comprises a collar means formed with a distal end positioned at the predetermined location.

18. A catheter assembly as recited in claim 14 wherein said elongated needle is formed of a distal portion of a given diameter that extends to the predetermined location and a proximal portion that extends from the predetermined location proximally to said operator means, said proximal portion having a greater diameter than said distal portion thereby to form a radially extending annular stop surface for engaging the proximal end of said shank means.

19. A catheter assembly as recited in claim 14 wherein said heating element includes an electrical element for selectively heating the selected tissue.

20. A catheter assembly as recited in claim 1 wherein said heating means includes an electrical element at the distal end of said catheter means for selectively heating the selected tissue.

\* \* \* \* \*

UNITED STATES PATENT AND TRADEMARK OFFICE
CERTIFICATE OF CORRECTION

PATENT NO. : 5,522,815

DATED : Jun. 4, 1996

INVENTOR(S) : Russell F. Durgin, Jr., Christopher A. Rowland, Roy H. Sullivan and Michael G. Vergano It is certified that error appears in the above-identified patent and that said Letters Patent is hereby corrected as shown below:

On the title page: Item [*] Notice

THE REFERENCE TO THE TERMINAL DISCLAIMER PATENT NUMBER 5,336,220 SHOULD READ PATENT NUMBER 5,336,222

Signed and Sealed this

Twenty-seventh Day of August, 1996

Attest:

BRUCE LEHMAN

Attesting Officer   Commissioner of Patents and Trademarks